United States Patent [19]

Beaudin

[11] Patent Number: 5,507,192
[45] Date of Patent: Apr. 16, 1996

[54] AUTOMATED GAS MEASUREMENT SYSTEM

[76] Inventor: Allen B. Beaudin, 5 Novilla, Laguna Niguel, Calif. 92677

[21] Appl. No.: 305,132

[22] Filed: Sep. 13, 1994

[51] Int. Cl.$^6$ .................................................. G01N 1/00
[52] U.S. Cl. ..................... 73/863.33; 73/863.83
[58] Field of Search .................. 73/1 G, 863.81, 73/863.82, 863.83, 863.84, 863.85, 863.86, 863.02, 863.03, 863.11, 863.12, 863.31, 863.33, 863.23, 863.24, 864.34, 864.81, 866.5

[56] References Cited

U.S. PATENT DOCUMENTS

| | | | |
|---|---|---|---|
| 3,784,902 | 1/1974 | Huber | 73/863.23 |
| 3,866,475 | 2/1975 | Thompson et al. | |
| 3,965,748 | 6/1976 | Boubel et al. | 73/863.23 |
| 4,051,731 | 10/1977 | Bohl et al. | 73/863.86 |
| 4,094,187 | 6/1978 | Navarre, Jr. | 73/864.34 |
| 4,566,342 | 1/1986 | Kutz | 73/863.03 |
| 4,578,986 | 4/1986 | Navarre | 73/863.83 |
| 4,630,482 | 12/1986 | Traina | |
| 4,747,581 | 5/1988 | Mailliet et al. | 73/863.11 |
| 4,779,466 | 10/1988 | Ramsner et al. | 73/863.12 |
| 4,937,461 | 6/1990 | Traina | |
| 5,077,480 | 12/1991 | Traina | |
| 5,297,432 | 3/1994 | Traina et al. | |
| 5,369,981 | 12/1994 | Merz et al. | 73/863.23 |

FOREIGN PATENT DOCUMENTS 868105  2/1953  Germany .............................. 73/863.81

OTHER PUBLICATIONS

Advertisement from United States, Inc.
40 C.F.R. Chapter 1 (Jul. 1, 1993 Edition) pp. 481–511.
40 C.F.R. Chapter 1 (Jul. 1, 1993 Edition) pp. 613–620.
40 C.F.R. Chapter 1 (Jul. 1, 1993 Edition) pp. 626–639.
KVB Product Profile for ECOSPEC Continuous Emissions Monitoring System.

*Primary Examiner*—Robert Raevis
*Attorney, Agent, or Firm*—Knobbe, Martens, Olson & Bear

[57] ABSTRACT

A automated system includes a set of probes used to conduct gas flow measurement and sample gas collection. A mobile unit transports the automated gas measurement system to the test facility, and the devices are easily and quickly assembled for testing at standard ports located around a smoke stack or exhaust duct. Two or four probes automatically and simultaneously perform leak checks, calibrations, and purging. At each of the traverse points to be tested, stepping motors provide precise automatic positioning with commands from programmable logic controllers interfacing with a computer located in the mobile unit. Measurement data is collected and sample analysis is performed automatically to generate a certification report in approximately one-third the time presently required.

20 Claims, 10 Drawing Sheets

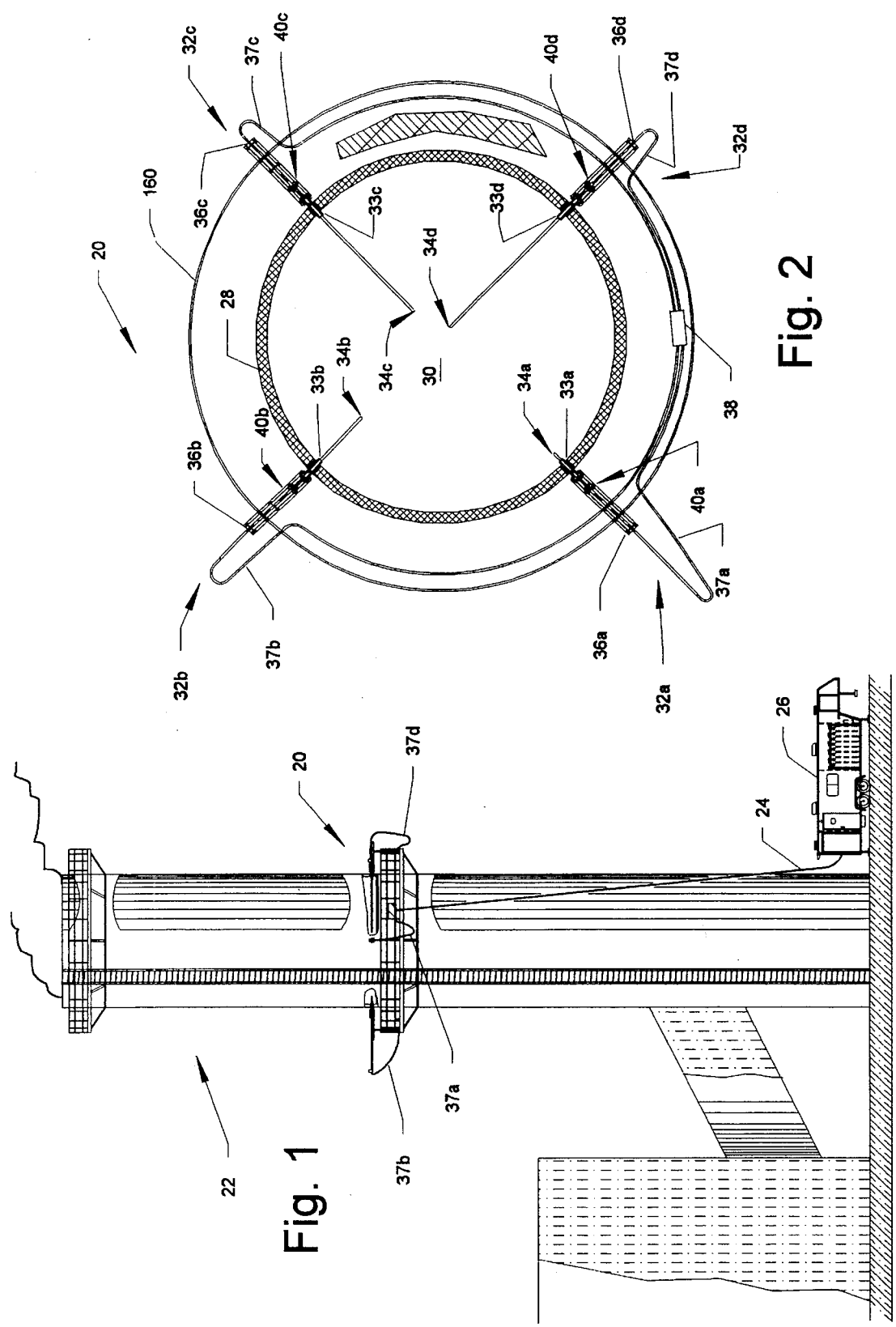

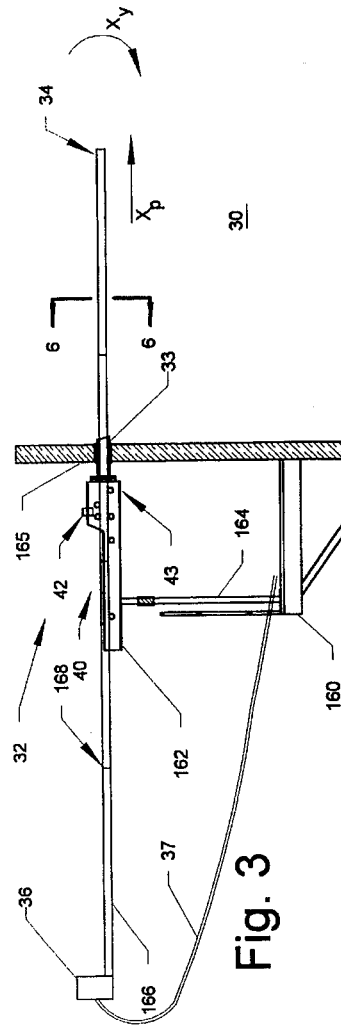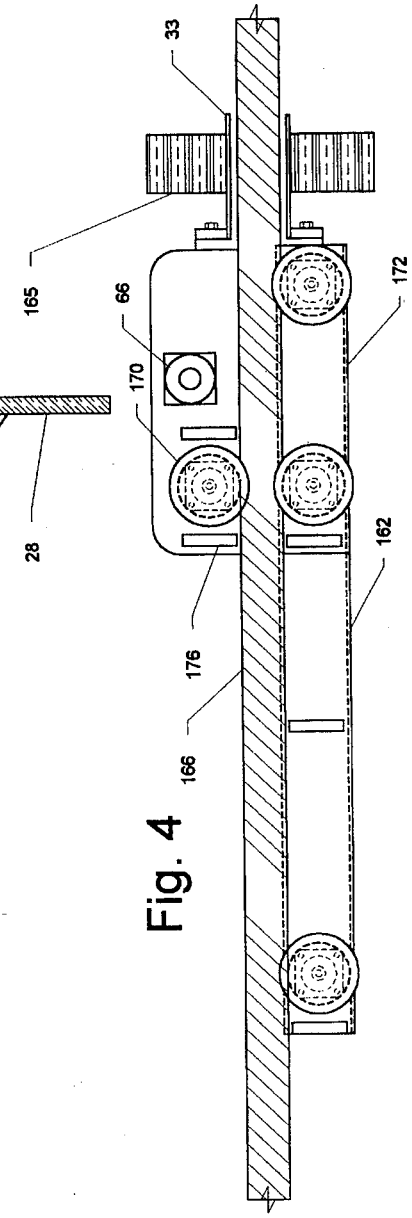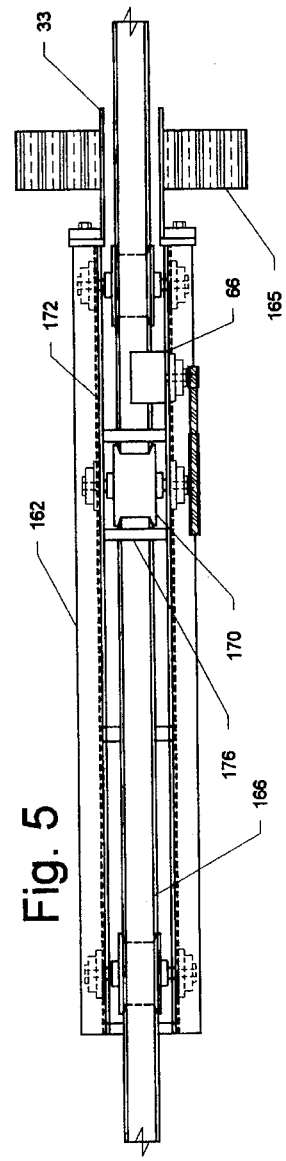

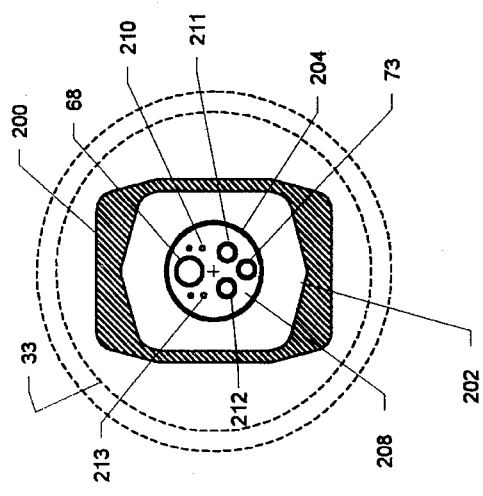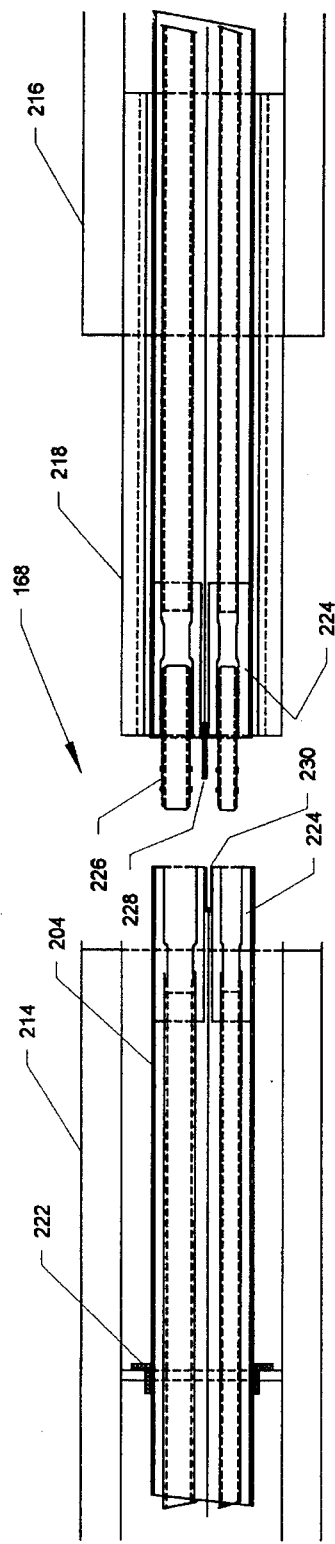

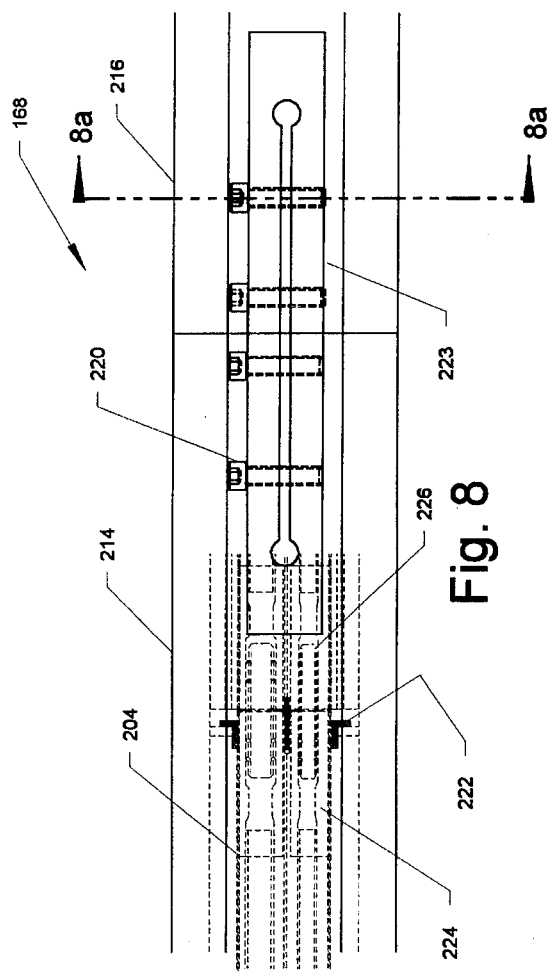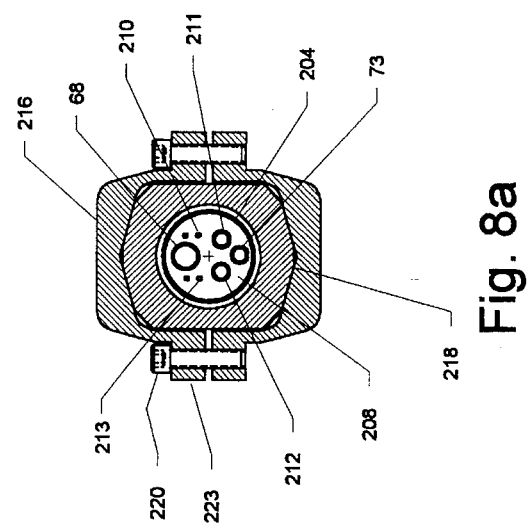

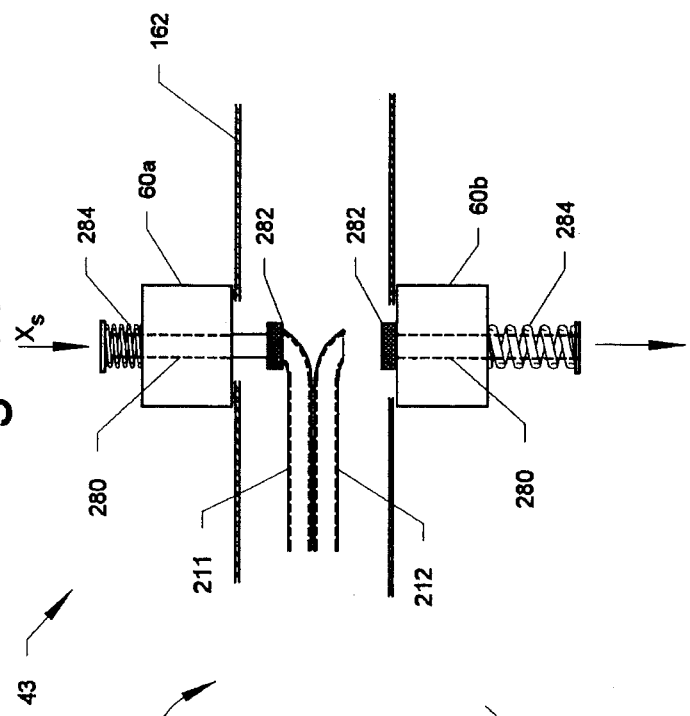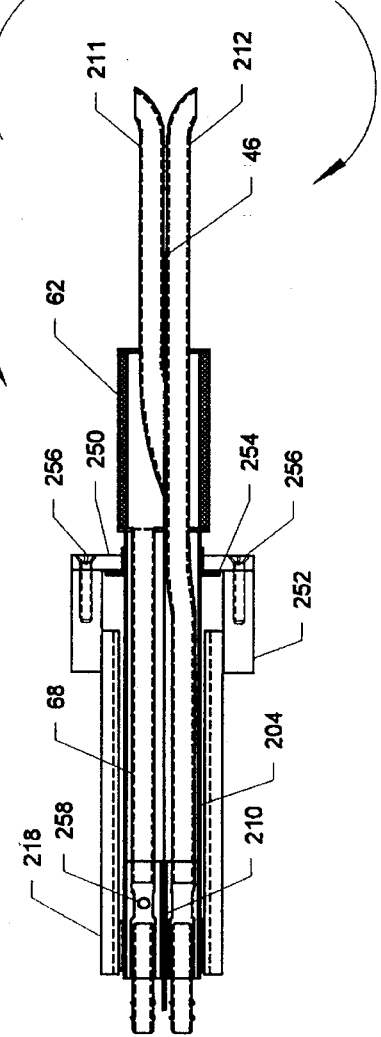

AUTOMATED GAS MEASUREMENT SYSTEM

BACKGROUND OF THE INVENTION

The present invention relates to gas measurement for constituent concentration and flow rate emitted from processes such as burning coal, oil, gas, wood, sewage, hazardous wastes, or venting from noncombustion processes.

The United States Environmental Protection Agency (EPA) has regulated techniques including reference methods for the measurement of gas constituent concentrations and flow from various processes. These techniques are found in Title 40 of the Code of Federal Regulations. The regulations detail the method to perform testing and report the results. This allows the emissions to be compared on an equal basis between different locations in the U.S. and among various industries.

Among the procedures to be followed are the measurement of pollutants for a volume of emitted gas at standard conditions. Briefly, standard conditions are determined by the gas flow temperature, "zero flow" pressure, atmospheric pressure, and calculated (average) molecular weight for the constituents to be measured. Also, a sample maintained at a temperature above the dew point of the relevant gases is required for determination of moisture content.

The devices used in sample collection must be chemically inert with respect to the sampled gases to ensure accuracy. The concern of the EPA is the mass quantity of an emitted gas and not the relative percentage in the total emission.

EPA regulations are included for both continuous emissions monitoring (CEM) and relative accuracy test auditing (RATA). CEMs are permanent, usually stationary instrument systems. RATA is a federally mandated, annual procedure to ensure the accuracy of the CEM reporting and is often conducted by a contracting service. The RATA testing is typically a lengthy process with a number of test procedures involving manual steps, with data from the tests subsequently input into a computer to generate an official report.

The recent enactment of the "Clean Air Act Amendments of 1990" has resulted in regulations that have increased the number of site emission sources requiring testing services. Currently, the available personnel to support these activities is critically low, and therefore emissions reporting is often delayed.

The typical RATA test requires 12 hours and a 3-person team. This team must climb to the test ports, which for a typical industrial smoke stack is located 100–500 feet above the ground. For power utilities, the smoke stack may be up to 46 feet in diameter; although, they are typically of 20–25 feet in diameter. The testing is conducted at 4 ports around the smoke stack, at a total of 24 radial traverse points within the smoke stack. These points are the centroids of 24 sites of equal area. The numerous gas sample collections and flow measurements require the team to repeatedly install and calibrate the devices, as well as perform leak checks and the necessary instrument purging between each traverse.

Recent advancements in testing techniques have allowed automation of some of these tasks and thus simplify the test procedures somewhat. For example, United Sciences, Inc., of Gibsonia, Pa., has designed a motorized, telescoping probe that automatically measures and records a velocity pressure at a specified traverse point in a smoke stack or exhaust duct. The probe has a reach or extension limited to 12 feet, and has a cost of several tens of thousands of dollars.

However, the numerous other gas measurements, and their leak checks and calibrations, must still be done manually. The operators are still required to manually reposition the single probe at each of the four ports of testing, as well as manually purge the probe between the pressure measurements.

SUMMARY OF THE INVENTION

The preferred embodiment of the automated gas measurement system of the present invention provides a portable combination or set of probes which are automatically positioned within the smoke stack. The probes perform flow measurement and convey test samples to a remote location, typically on the ground in a trailer, so that after the probes are temporarily installed, the entire test procedure can be conducted from the remote location by a single operator.

System Highlights

The preferred embodiment of the automated gas measurement system of the present invention provides the following important features: 1) a set of automatically positioned probes linked to a computer remotely located in a mobile unit containing test and control equipment; 2) a movable probe assembly performing automated flow measurement and sample collection, with quality assurance features such as automatic purging (auto-purging); 3) automatic, on-site data collection and report generation by user-friendly software resident in the control computer; and 4) the ability to easily update or modify both hardware and software to keep pace with changes in EPA regulations and available technology.

As mentioned, a first important feature of the present invention is an automated set of probes for simultaneous flow measurement and sample collection around a smoke stack or exhaust duct. The system utilizes a trailer or mobile unit, as the remotely located control station. The preferred use of 2 or 4 probes, depending upon the diameter of the smoke stack to be tested, reduces the required testing time to approximately 4 hours, or ⅓ the current testing time. The system automation provides standardization and repeatability with minimal operator intervention required.

Once the mobile unit of the system has been temporarily installed at the test facility, and the two or four probes mounted at the test ports, only a single operator is required to initiate and monitor the actual testing. In a preferred embodiment, the use of a conventional gas divider reduces the number of gas cylinders required to be transported. The further use of conventional sample conditioners, collection lines or tubes, and gas analyzers provide familiarity for the operator and ready availability for replacements. Control of the test equipment is provided through a programmable logic controller (PLC) and computer colocated in the mobile unit, and which employ a user-friendly high level language. A video library provides on-site troubleshooting for the operator, and procedure review, if necessary.

A second important feature of the present invention is that each movable probe assembly automatically performs leak checks and calibration, and auto-purging of the filter and pitot tube assembly located at the proximal end of each probe. In the preferred embodiment, a sintered metal filter is used in the sample gas collection, and a standard type S (Stausscheibe or reverse type) pitot tube is used for gas flow measurement. While auto-purging and leak checking are presently available for stationary probes, the system of the present invention is the first to perform auto-purging of a movable probe. The quality assurance features of leak checks, calibrations, and auto-purging further reduce the requirement for operator expertise and intervention.

Each probe is independently operated, with separate quality assurance mechanisms and connections to the operator control station located in the mobile unit. A "remote" PLC located near the probe assemblies interfaces with the PLC in the mobile unit, and issues commands to each of the probe assemblies.

The probe length is segmented and adjustable for a total extension up to 25 feet to accommodate the largest of smoke stack diameters. This length is achieved with minimized bending through the use of an aluminum housing around the aluminum probe shaft. The preferably 2.5"×3" octagonal housing is sized for use with the standard 4" smoke stack port. For the typical utility industry smoke stack 24 feet in diameter, a set of two probes, each of maximum length and spaced 90 degrees apart, can easily be used to cover the 24 test points within the smoke stack. The sites for a cylindrical smoke stack are formed from 4 quadrants of a horizontal cross-section, with each quadrant divided into 6 equal site areas. Thus, two probes in adjacent quadrants can each extend the width of the smoke stack in order to test all four quadrants. For larger diameter smoke stacks, four probes would be used.

A third important feature of the preferred embodiment of the present system is that CEM data input at the test facility is accomplished through use of a scanner and optical recognition software, downloading from a diskette, or "prompted" user keyboard entry. The testing is initiated from the computer in the mobile unit, which provides the interface with the PLCs. Various commercial man-machine interface (MMI) software may be used, such as "Factory Link" by U.S. Data or "Wonderware" or "Aimax". The comparison of the CEM and testing results are automatically processed by the computer while on-site. The gas and flow analysis reporting is done using a reference database and various templates or macros for tabular, graphic, and text formatting. A preliminary or final certification report may be generated to conform with regulatory use, either as a hard copy or as an electronic data report (EDR).

Significant advantages of the automated gas measurement system of the present invention are a reduction in the personnel required to perform emissions testing and reporting, as well as a reduction in the actual testing and data conversion time. The time savings translates into cost savings for a utility company, since a reduced operating load is usually required during testing. In addition, another important feature of the present invention is that any future changes in EPA regulations, available test technology, or customer needs, are readily incorporated into the measurement and reporting performed by this automated system. Further advantages and applications will become apparent to those skilled in the art from the following detailed description and the drawings referenced herein.

BRIEF DESCRIPTION OF THE DRAWINGS

FIG. 1 is an elevational view of a preferred embodiment of the present invention, illustrating the set of automated probes equidistantly located at the test ports of a smoke stack and also showing the associated portable control and test equipment.

FIG. 2 is a top plan view of the preferred embodiment of FIG. 1, illustrating the positioning of the four automated probe assemblies about the smoke stack.

FIG. 3 is a side view of a typical probe assembly in the preferred embodiment of the present invention, illustrating the combination of probe segments, end housing, pitot tube assembly, and support as temporarily installed at each port of the smoke stack.

FIG. 4 is an elevational view of the probe support of FIG. 3, illustrating the system of roller bearings surrounding the probe.

FIG. 5 is a top plan view of the probe support of FIG. 3, further illustrating the roller bearings.

FIG. 6 is a transverse cross-section of the probe along lines 6—6 of FIG. 3, illustrating the preferred shape of the probe housing.

FIG. 7 is a longitudinal cross-section view of the probe segment connections of FIG. 3, illustrating the tube and electrical connections prior to mating.

FIG. 8 is a longitudinal outside view of the probe segment connections of FIG. 3, illustrating in phantom the tube and electrical connections after mating.

FIG. 8a is a transverse cross-section along lines 8a–8a of FIG. 8, illustrating the clamping of a male fitting within a female portion of the probe segment connections.

FIG. 10 is a longitudinal cross-section view of the pitot tube assembly of the preferred embodiment of the present invention, illustrating the proximal end of the probe prior to assembly and installation.

FIG. 11 is a cross-section view of the pitot tube assembly of FIG. 10, illustrating the method of sealing the heads of the pitot tubes during a leak check.

DETAILED DESCRIPTION OF THE INVENTION

Overview

Figure 9:
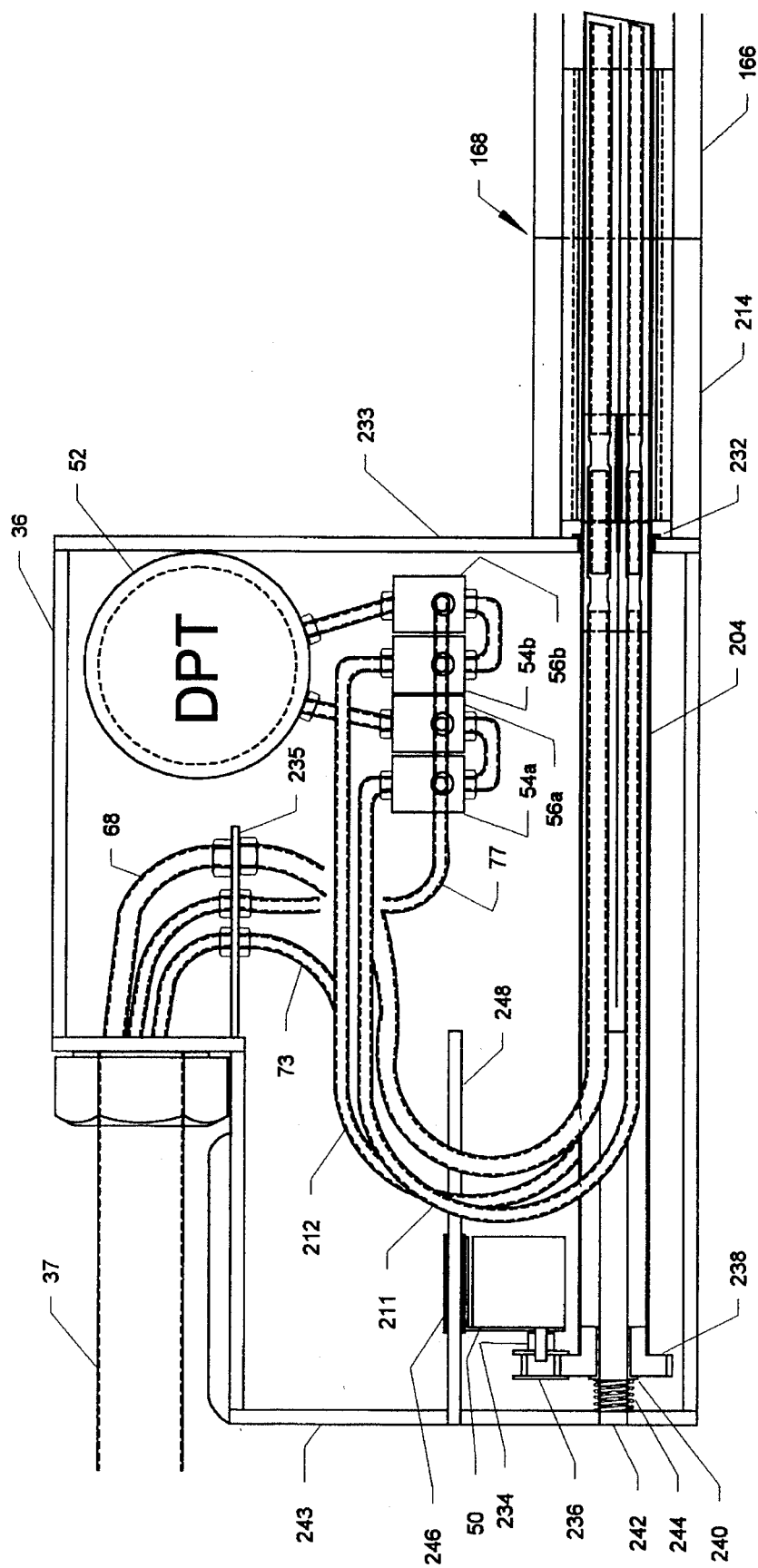
FIG. 9 is a longitudinal view of the end housing of the probe assembly of FIG. 3, with half of the outer casing removed to show the yaw control and flow measurement devices.

The preferred embodiment of the present invention utilizing four probes in a system or probe set is shown in FIG. 1, referenced generally by numeral 20. A combination of valves, motors, transducers, a pitot tube assembly, and a filter, comprise each probe assembly 32, which are designated as 32a–d. The probe assemblies 32a–d include position sensors and are preferably positioned by stepping motors. The probe assemblies 32a–d are controlled using an indexing module that is part of a remote PLC 92 which is in communication with a PLC 156 in a mobile unit 26. A junction box 38 located near the set of probes 20 on a smoke stack 22 contains the remote PLC 92, a heater, air and gas hoses, an air storage tank 89, and valves corresponding to each of the four probe assemblies 32a–d.

The automated probe set 20 of the present invention is located approximately 5 "diameters" from the inlet of the smoke stack 22, along its height. Although four probes 32a–d are shown comprising the probe set 20, it is to be understood that more or less may be used in the present invention. As can be seen in FIG. 2, for the "typical" probe assembly 32a, a line 37a is used to route the various air and gas tubes from the probe assembly 32a to the junction box 38. A tube bundle 24 including an air tube for purging, a sample gas tube, and a calibration gas tube extends from the junction box 38 down to the trailer or mobile unit 26. The mobile unit 26 contains, among other devices, gas cylinders and gas analyzing equipment, which will be described in detail below.

The specific configuration of the probe set 20 of the preferred embodiment is seen in FIG. 2. Here, a view downward is shown, from just above the probe set 20 on a smoke stack wall 28, to illustrate the positioning of each probe assembly, such as 32a, through a "standard" port opening 33a, which is typically 4" in diameter. Located proximally at the end of the probe assembly 32a—that is, within an interior 30 of the smoke stack 22—is a pitot assembly 34a. An end housing 36a of the probe assembly 32a is shown at a distal end, and the line 37a extending from the end housing 36a is connected to the junction box 38, along with lines 37b–d of the other probe assemblies 32b–d. Although only one junction box 38 is shown, it is to be understood that more than one may be used in alternate embodiments of the present invention. As will be described in further detail below, support structures 40a–d, indicated in FIG. 2, are used for support of the probe assemblies 32a–d during installation and testing.

In the preferred embodiment of the present invention, and as shown in FIGS. 1 and 2, each of the four equally spaced motorized probe assemblies, such as 32a, extends the pitot tube assembly 34a through the test port 33a into the smoke stack interior 30 for flow measurement. Position sensors for the longitudinal and rotational displacements of the probe 32a relay information to the remote PLC 92, which transmits signals to the stepping motors for precise advancement of the set of probe assemblies 20. Based on data entered during the test setup, the exact traverse point coordinates have been predetermined for use by the remote PLC 92.

The probe assemblies 32a–d are each controlled for axial or longitudinal movement as well as rotational or yaw positioning. As mentioned above, the remote PLC 92 provides the control commands, and for each probe assembly, such as 32a, a system of timing belt-driven roller bearings controlled by one of the stepping motors positions the probe assembly 32a within the smoke stack interior 30. The remote PLC 92 also commands a pair of spur gears located in the end housing 36a, at the distal end of the probe assembly 32a, to provide rotational or yaw positioning of the pitot tube assembly 34a, which is located on the opposite, proximal end of the probe assembly 32a. These control mechanisms are described in further detail in connection with FIGS. 4, 5, and 9. And, although yaw control is described to be located at the distal end of the probe 32a, it will be obvious to those skilled in the art that another location may be chosen.

As indicated in FIG. 2, at each traverse within the smoke stack 22, the position, gas velocity, and temperature are automatically measured and recorded. For the probe 32a, a conventional type S pitot tube 44a of the pitot assembly 34a measures the gas velocity or impact pressure using a delta pressure transducer (DPT) 52. The DPT 52 determines the difference or delta between the pressures measured by the two heads of the tube, one head pointed generally upstream, and the other head pointed 180 degrees away, generally downstream. The null point of the flow is determined first, where the measured delta is zero. Then the maximum flow velocity is measured and is known to be at 90 degrees to the null point. A standard RTD thermocouple 46 adjacent the pitot tube 44a measures the gas temperature. Temperature information from the pitot tube assemblies 34 is stored continuously, in analog form, and tagged for time and probe identification for later reference and use.

The sampling procedure used by the present invention is a standard extraction method which withdraws gas from a stream comprised of post combustion products and filters out any dust. Preferably, a sintered metal filter 62 is used; although, other filters of finer grade may be substituted. The gas sample is conveyed within heated tubing to the test equipment in the mobile unit. This procedure and its devices are described in detail below with respect to FIGS. 12–14; however, it is readily apparent that any conventional sampling method may alternately be used.

The automatic calibration of the gas sample analyzers used by the present invention is one of the quality assurance (QA) features of the present invention. By way of specific example, sampling procedures required by the EPA require performing reference methods for quality assurance. A significant feature of this invention is that such reference methods are performed automatically.

Additional QA is found on the probe assembly itself, such as 32a, and includes calibration, leak checks, and automatic purging (auto-purging) of a sample tube 68a and the pitot tube 44a. During a leak check the two awkwardly shaped heads of the pitot tube 44a are sealed using rubber plugs. A solenoid and plunger mechanism is used to force a plug against the face of each tube. Compressed air is used for the auto-purging, routed from the mobile unit 26 to the sample tube 68a and also to the pitot tube 44a.

Not illustrated in the drawings are the electrical cables which are routed from the mobile unit 26 to the junction box 38, from the box 38 to the structures 40a–d, and from the structures 40a–d to the end housings 36a–d. These cables include lines for power, sensor information, and temperature readings. Conventional electrical plug connectors are used at each of the unit 26, box 38, structures 40a–d, and housings 36a–d.

For simplicity, from here on, the "a", "b", "c" and "d" designations will be omitted in referring to those elements common to each probe assembly 32 (such as 33a–d, 34a–d, etc.), except as necessary for clarity.

Typical Probe Assembly

FIG. 3 illustrates the typical probe assembly 32 when assembled and operable. Generally, the probe assembly 32 of FIGS. 2 and 3 is designed to provide an unsupported span of up to 25 feet, positioned through the standard 4-inch port 33. An aluminum outer construction enables use in temperatures up to 400° F.

The pitot assembly 34 is located at the proximal end of the assembly 32, and the end housing 36 is shown on the distal end. The line 37 for this assembly 32 extends from the end housing 36 onto a conventional smoke stack platform or walkway 160, where a support body or housing 162 of the probe assembly 32 is also mounted thereon. An adjustable support strut 164 provides substantially horizontal positioning of the assembly 32. The erected structure of the probe assembly 32 will preferably incorporate a slight upward bend to counteract gravitational effects tending to weigh the assembly 32 downward. It will be obvious to those skilled in the art that other support members, adjustable or fixed, may be substituted in the present invention.

As shown in FIG. 3, the proximal end of the support housing 162 abuts a flange 165 surrounding the port opening 33. In the preferred embodiment, the probe assembly 32, as installed, is comprised of up to 4 individual segments 166 approximately 4½ to 7 feet long, according to the length required for the diameter of the smoke stack being tested. The number of possible segments 166, and their individual lengths, may be varied and are understood to be within the scope of the present invention. Each segment 166 is mated during assembly at the connections, generally referenced by the numeral 168, which will be detailed below.

Probe Support Structure

Figure 12:
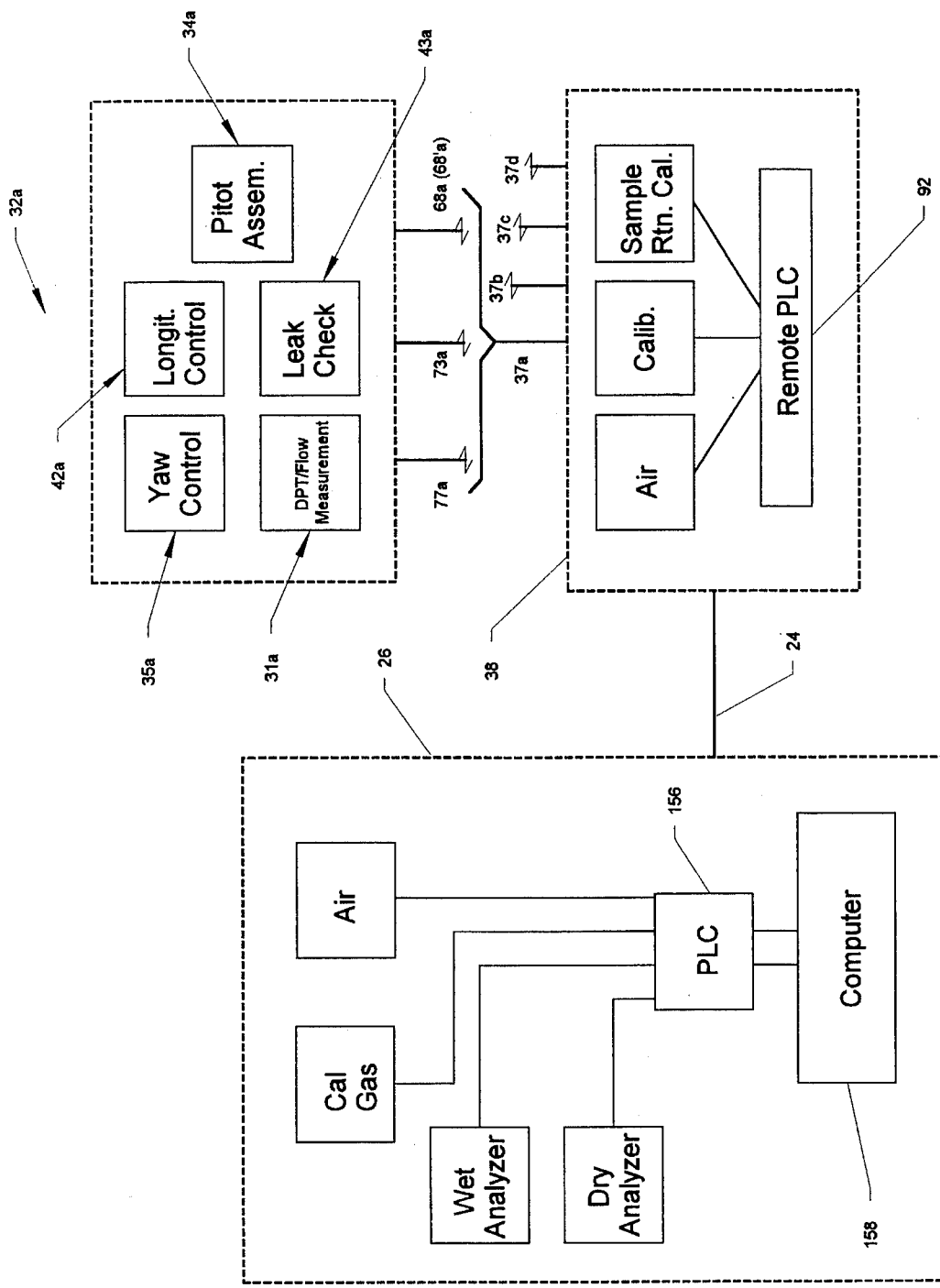
FIG. 12 is a simplified schematic of the devices of FIGS. 13 and 14, illustrating the relationships between the devices contained on the probes and the devices located in the mobile unit.
Figure 13:
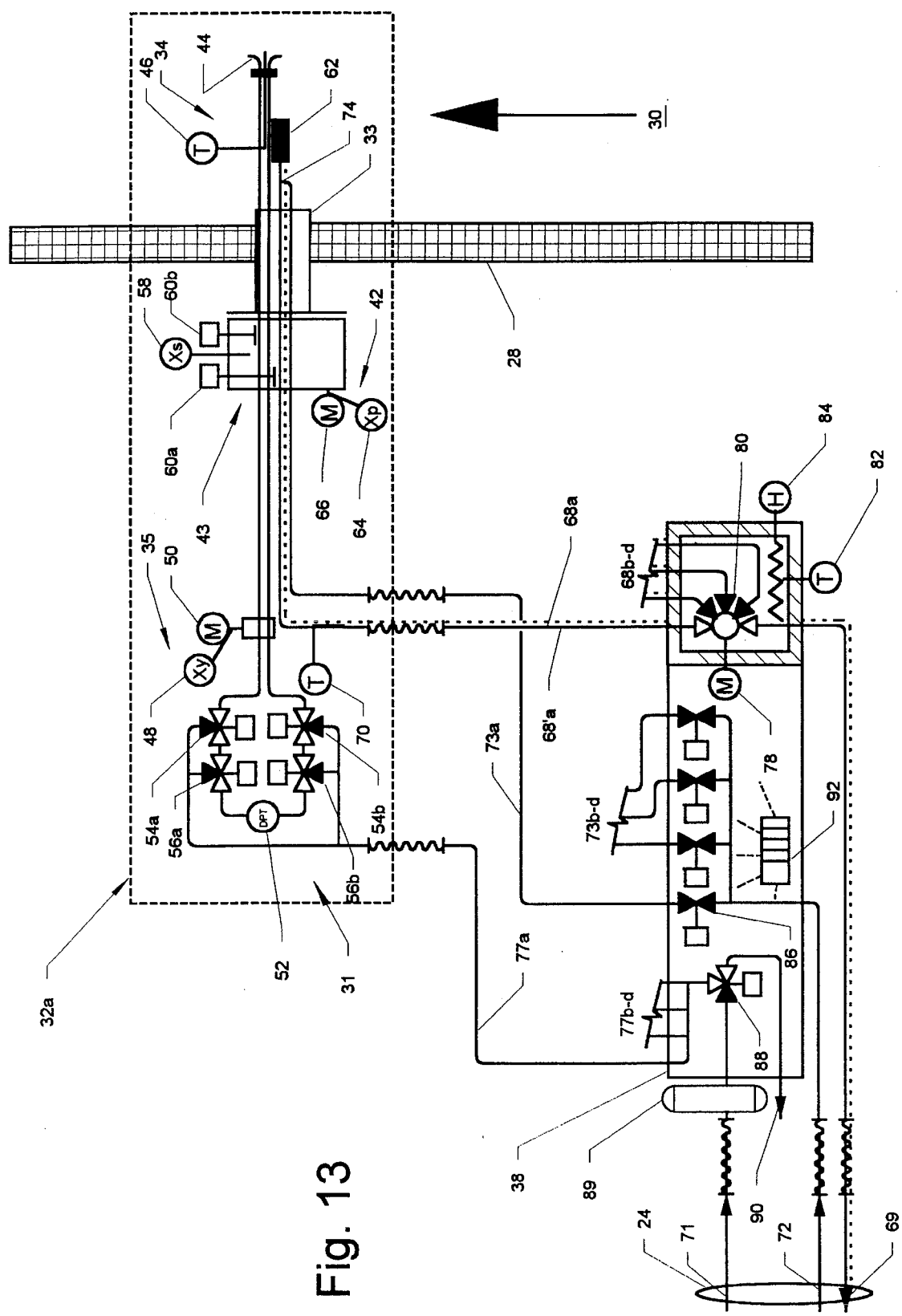
FIG. 13 is a schematic of the typical probe assembly of the FIG. 3, as connected to the junction box and including air, calibration gas, and sample gas tubes.

FIGS. 4 and 5 show in greater detail the construction of the support housing 162 and the use of roller bearings 170 in the longitudinal positioning and support of the probe assembly 32 prior, and are described below. The mounting of the probe assembly 32 prior to testing includes bolting the support structure 40 to the flange 165 surrounding the port opening 33 of the smoke stack 22 (see FIG. 3). The adjustable strut 164 of the support 162 is bolted onto the walkway 160. A stepping motor 66 for axial or longitudinal positioning control of the probe 32 is included in the proximal portion of the support housing 162. (As indicated in FIGS. 12 and 13, a stepping motor 50 used for rotational or yaw positioning of the pitot tubes 44 in the gas flow of the stack interior 30 is contained within the end housing 36 of the probe assembly 32; although, the motor 50 may be contained elsewhere on the assembly 32.) While stepping motors 50, 66 are described, other means well known to those skilled in the art may be substituted to provide longitudinal or yaw positioning in the system of the present invention.

Referring to FIGS. 4 and 5, the roller friction system of the preferred embodiment includes at least three lower and one upper roller bearing 170 which are contained within the probe control housing 172. The roller bearings 170 take both upward and downward loads resulting both from the static weight of the assembly 32 and from the longitudinal or rotational motion. The roller bearings 170 are driven by a belt (not shown) coupled to the motor 66. The high output of the motor 66 is preferably linked to a speed reducer (not shown) to match the slower roller speed. Preferably, a loose gear system (not shown) is added for safety and to prevent slippage.

The roller bearings 170 in the control housing 172 are flanged to accept side thrust forces and provide lateral alignment. Preferably, three additional, lower bars 176 are provided on the distal portion of the support 162. These bars 176 provide support primarily during assembly of the probe 32. In alternate embodiments, there may be more or less rollers or bars 170, 176 located in the control housing 172 or on the support housing 162. Alternate mechanisms known to those skilled in the art may also be used in place of the friction roller bearing system described herein. The rollers 170 in FIGS. 4 and 5 are preferably formed of aluminum which is coated with an elastomer having high resistance to hydrocarbons, steam, water, and solvents, such as the copolymer Viton by DuPont.

Not shown in the support structure 40 of FIGS. 4 and 5 are the pitot cap assembly 43 and a longitudinal position sensor ($X_p$) 64. However, the cap assembly 43 is described below in conjunction with FIG. 11. The position sensor 64 (referenced schematically in FIG. 13) provides information on the probe's axial or longitudinal position into/out of the smoke stack 22, as indicated in FIG. 3. The remote PLC 92 uses this information in commanding the motor 66 for testing at each traverse point.

Probe Construction

Referring now in detail to FIG. 6, a cross section is shown of a typical probe segment 166 of the preferred embodiment of the present invention. Here, it can be seen that an outer aluminum housing 200 is of a generally octagonal shape, with a similar octagonal interior opening 202. The preferred exterior dimensions of the outer housing 200 are 2.5 inches by 3 inches, which conforms to use with standard port openings 33 having 4-inch diameters (shown in phantom in FIG. 6). The shape and relative dimensions of the outer aluminum housing 200 of the probe 32 are designed to maximize the area moment of inertia, I. It is known to those skilled in the art that the bending deflection, f, is inversely proportional to the area moment of inertia, or $f=[(W * l^3)/(k * E * I)]$. Therefore, maximizing the area moment of inertia serves to minimize the deflection along the probe assembly 32. Further, the tapered portions of the upper and lower flanges of the octagonal shape allow access for positioning of the connections and provide lateral rigidity. However, while this shape is preferred, other shapes may be used in other embodiments of the present invention.

The yaw shaft 204 of the probe assembly 32 is comprised of a hollow cylinder, and preferably of 1¼-inch diameter 20-gauge aluminum. The yaw shaft 204 has an interior space 208, which encompasses a thermocouple wire 210, pitot tubes 211, 212, and a heat trace cable 213, as well as the sample tube 68 and a calibration (cal) gas tube 73.

Probe Connections/Assembly

Referring now in detail to FIGS. 7 and 8, the preferred embodiment of the connection 168 for two segments 166 of the probe assembly 32 is shown, wherein a female portion 214 of the segment 166 mates with a male portion 216. A male fitting 218 is dimensioned for a loose fit within the female portion 214. The male fitting 218 is precision machined and then fastened to the male portion 216 of the connection 168. Screws 220 are utilized to clamp and assure a tight fit of the male fitting 218 within the female portion 214. Teflon bearings 222 are proximally located, within the female portion 214, and allow the yaw shaft 204 to slide freely in the longitudinal direction.

Connecting plugs 224 at the ends of the yaw shaft 204 are located on each male 216 and female 214 end of a segment 166, as shown in FIG. 7. The plugs 224 are comprised of male and female types which are pressed together. The plugs 224 are made of a thermopolymer, such as DuPont Teflon and are press fitted into the yaw shaft 204. The connections for each tube 68, 73, 211, 212 to the connecting plug 224 are individually made, and connected using a high-temperature press-fit infusion technique known to those skilled in the art. The electrical connections 228, 230 are press fitted into the plugs 224.

These plugs 224 connect stainless steel inserts 226 that contain O-rings (not shown) for a tight seal, and which correspond to each tube 68, 73, 211, 212, as well as to respective male 228 and female 230 electrical connectors.

The male fitting 218 is then inserted into the female portion 214, and tightening of the screws 220 over slotted, bar-like extensions 223 of the portions 214, 216 completes the connection, as shown in FIGS. 8 and 8a. As seen more clearly in FIG. 8a, these extensions 223 are formed on both of the vertical, outer sides of the portions 214, 216. The slots allow the compression of these sides by the tightening of the screws 220 such that the male fitting 218 is tightly clamped.

The connection procedure is similarly performed at the end housing 36 and pitot assembly 34, at the distal and proximal ends of the probe assembly 32, respectively, as described below. It is to be noted that alternate sealing connections for any part of the probe assembly 32 may be used in other embodiments of the present invention.

End Housing

FIG. 9 illustrates the contents of the end housing 36. The tubes 68, 73, 211, and 212 extend from the distal end of the probe assembly 32 through an opening 232 on the lower portion of the proximal or front panel 233 of the housing 36. A female portion 214 is attached at the front panel 233 to provide connection to the probe segment 166, in the manner described above. The tubes 68, 73, 211, and 212 exit the shaft 204, and holders 235 are used to position the tubes near the entry into the line 37, which is located at the upper distal end of the housing 36.

It is seen in FIG. 9 that the pitot tubes 211, 212 are routed to solenoid valves 54, 56, along with an incoming air tube 77. The DPT 52 associated with the pitot assembly 34 is shown; however, the thermocouple 210 and heat trace 213, as well as a yaw position sensor ($X_y$) 48 are not shown, although they are also contained within the housing 36. The yaw position sensor 48, described below with the remote devices, measures the angular displacement or rotation of the pitot tube assembly 34, as indicated in FIG. 3.

The yaw motor 50 provides the necessary rotation about the longitudinal axis of the pitot assembly 34 through the use of spur gears 234, 236, as shown in FIG. 9. The larger spur gear 236 includes a hub 238 which is machined to fit tightly within the shaft 204. The hub 238 contains a Teflon flanged sleeve bearing 240, within which is inserted a bar 242 that extrudes from the distal or rear panel 243 of the housing 36. A spring 244 is used to provide constant tension on the yaw shaft 204. For ease in assembly, the motor 50 is made movable parallel to the shaft 204 by a guide plate 246 which rides along a rod 248. To eliminate the need to realign the gears 234, 236 between test points, the motor spur gear 234 is flanged to maintain contact and alignment with the yaw spur gear 236.

Pitot Tube Assembly

The construction of the pitot assembly 34 is shown in greater detail in FIG. 10. A plate 250 is attached to the end (male) connection 252 of the pitot assembly 34. The male portions 218, 252 are preferably manufactured of all metal for manufacturing ease. Flanged sleeve bearings 254 are used at the end connection 252 to take the loading associated with the weight and yaw motion (rotation) of the pitot assembly 34. Screws 256 provide attachment of the plate 250 and bearings 254 onto the end connection 252. During assembly, the male fitting 218 of the end connection 252 is mated in a procedure similar to that previously described.

The sintered metal filter 62 is open on its distal end to the sample tube 68, while the pitot tubes 211, 212 and thermocouple 46 are welded on the opposite, proximal end of the filter 62. A bore hole 258 is located near the distal end of the pitot assembly 34, which allows the purge air or cal gas from tube 73 (hidden from view in FIG. 10) to flow into the sample tube 68, at a junction 74. Cal gas may flow out the filter 62, which serves to prevent sampled gas from flowing into the tube 68 during calibration. Sealing of cal gas flow is accomplished by a valve 86 located within the stack junction box 38, which ensures that during sample collection there is no dilution of the sample gas by cal gas. The bore hole 258 construction was chosen to reduce the number of tubes assembled to the filter 62. However, the method of injecting cal gas at the filter 62 could be substituted in an alternate embodiment of the present invention.

As described above, for flow measurement the pitot tubes 211, 212 are first positioned to determine the zero flow angle, which is the angle where the DPT 52 reads zero for the difference in the upstream and downstream pressures within the stack interior 30. A 90 degree rotation of the assembly 34 by a yaw control unit 35 provides proper positioning to measure the maximum flow at the traverse point, which is used to determine the total mass flow of the constituents, as required by the EPA.

Leak Checks

To ensure accuracy and proper operation of the pitot tube assembly 34, the pitot tubes 211, 212 are sealed for a quality assurance check. The proximal end of the probe 32 is automatically retracted for the leak checks into the support housing 162, where the pitot cap assembly 43 is located.

FIG. 11 illustrates the preferred method of sealing the awkwardly shaped heads of the pitot tubes 211, 212 during the automated leak checks. However, other sealing means known to those skilled in the art may alternately be used. Here, solenoids 60a,b surround metal shafts 280 which contain rubber plugs 282 on their interior ends. When activated, the solenoids 60a,b drive the shafts 280 such that the plugs 282 sealingly engage onto the heads of the pitot tubes 211, 212. In FIG. 11, the upper solenoid 60a is shown activated, with the plug 252 in place over the head of the tube 211. The lower solenoid 60b is shown in a relaxed state, where a spring 254 provides tension to position the rubber plug 252 radially outward from the housing 162. A position sensor $X_s$ 58 monitors the engagement or deactivation of the solenoids 60.

Operation

FIG. 12 is a simplified schematic illustrating the relationships between the "remote" devices controlled by the computer 158 via the remote PLC 92, and the "local" devices directly linked to the PLC 156 and computer 158 in the mobile unit 26. The typical probe assembly 32 is represented, and its associated remote devices—generally referenced as 31, 34, 35, 42, and 43—are indicated. The sample tube 68 (also used as a cal gas return tube 68'), the cal gas tube 73, and the air tube 77, as well as electrical connections (not shown), are contained in the line 37a for conveyance to/from the junction box 38.

Control algorithms resident in the computer 158 issue commands to the PLC 156. The PLC 156 commands the remote PLC 92 to connect a selected line 37 (such as 37a, in its turn with lines 37b, 37c, and 37d) to the main air and gas tubes contained in the tube bundle 24, for conveyance to/from the local devices located in the mobile unit 26. The PLC 156 further issues commands to the local devices to perform the test procedures, as indicated in FIG. 12.

Remote Devices

Referring now to FIG. 13, the probe assembly 32a and the junction box 38, are shown in greater schematic detail. A probe control unit 42 is collocated with the pitot cap assembly 43 within the probe support structure 40. The probe position sensor 64, shown in FIG. 13, is located in the probe control unit 42, as is the motor 66. The sensor 64 is used to relay information on the probe's axial or longitudinal position (into/out of the smoke stack 22, as indicated in FIG. 3) to the remote PLC 92.

As seen in FIGS. 2 and 13, and previously described, the type S pitot tube 44 is located on the proximal end of the probe assembly 32, which is inserted into the gas stream within the smoke stack interior 30. The RTD thermocouple 46 is also located at the proximal end. The angular displacement or rotation of the pitot assembly 34 about the probe's longitudinal axis is measured by the yaw position sensor 48, which is contained in the yaw control unit 35 and provides yaw position feedback to the remote PLC 92. Also contained in the control unit 35 is the yaw motor 50 for the rotation of the pitot assembly 34, as indicated in FIGS. 3 and 10.

As described previously, the DPT 52 is part of the control unit 35, which further includes solenoid valves 54a,b. Isolation solenoid valve 56a is used for calibration of the DPT 52. The DPT calibration forms no part of the present invention and will not be described in further detail. Isolation solenoid valve 56b is used for purging of the pitot tubes 211,212. The pitot cap assembly 43 includes the solenoid position sensor ($X_s$) 58 for feedback during the leak check of the pitot tube 44; that is, the positions of the solenoids 60 are monitored during the leak check and after, as indicated in FIG. 11. The operation of the pitot cap solenoids 60 were described in greater detail in connection with the leak check QA feature of the present invention.

As shown in FIG. 13, the heated sample tube 68 extends from the filter 62, through the probe 32, to the junction box 38. The temperature transducer 70 monitors the elevated temperature required to prevent condensation within the sample tube 68. Also shown in FIG. 13 is the cal gas return tube 68', which is simply the sample tube 68 when used during the "remote" calibration of the sampling equipment. The flow of the heated sample gas in tubes 68a–d is regulated through means provided in the junction box 38, described in detail below. The sample tube 68 is preferably a ⅜" diameter Teflon hose. The sampled gas is conveyed to the mobile unit 26 from the junction box 38 through the main sample tube 69.

Calibration gas is conducted through the tube bundle 24 from the mobile unit 26 in the main cal gas tube 72. FIG. 13 illustrates the main gas tube 72 extending to the junction box 38 for cal gas flow into the appropriate cal gas tube 73. The cal gas tube 73 joins the return tube 68' at the T-junction 74. The bore hole 258, described above for FIG. 10 (illustrating the pitot tube assembly 34), is located at the junction 74 and provides the means for flow from the cal gas tube 73 to the cal return tube 68' The cal gas tube 73 is preferably comprised of a ¼-inch diameter Teflon hose. The main purge or air tube 76 extends from the mobile unit 26 through the tube bundle 24, and the main air tube 76 and individual air tubes 77 are similarly regulated through means within the junction box 38.

As described previously, power and electrical connections for the various thermocouples, solenoids, motors, and valves are routed through separate cables. The cables extend between the end housings 36 and structures 40, the structures 40 and junction box 38, and the junction box 38 and mobile unit 26. Each cable contains only the electrical connections required between each point, with the structures 40 serving as a relay point for the housings 36.

Junction Box

The portion of FIG. 13 showing the schematic of the junction box 38 will now be described. The four sample/cal return tubes 68a–d/68'a–d are selectively controlled through a motor 78 and a 5-way motorized valve 80. A temperature controller 82 regulates the heating of the sample tubes 68a–d by a heater 84. The four cal gas tubes 73a–d are controlled through solenoid valves 86a–d. The four air tubes 77a–d employ a single solenoid valve 88, and the main air tube 76 may also be regulated to exit through a vent 90. An air storage tank 89 is preferably provided adjacent the junction box 38; although, its use is optional. As mentioned, the remote PLC 92 is located within the junction box 38 for monitoring and control of the remote devices, and for communication with the PLC 156 located in the mobile unit 26.

Mobile Unit

Figure 14:
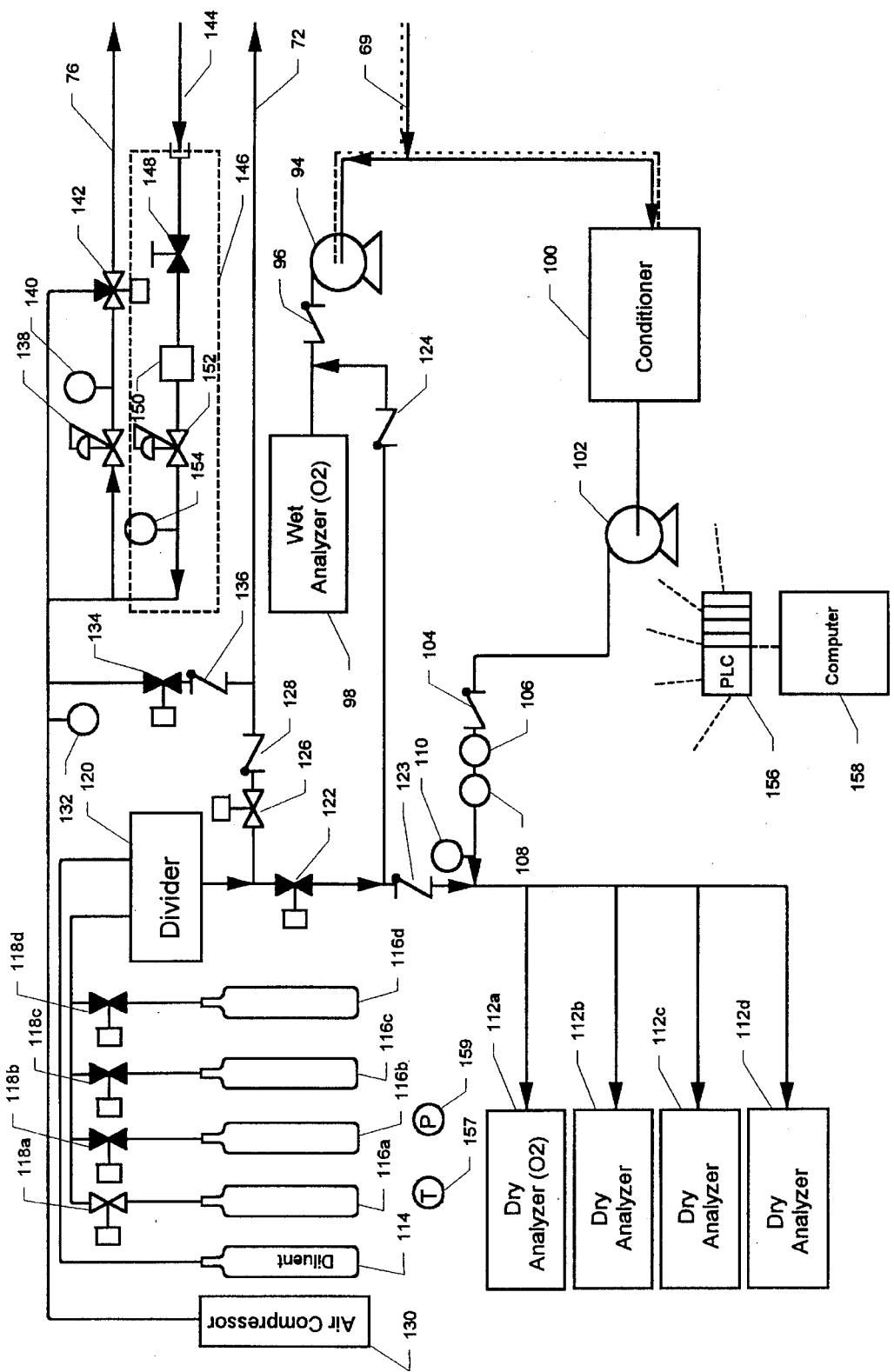
FIG. 14 is a schematic of the devices contained in the mobile unit of the present invention, including a gas divider, a sample conditioner, and gas analyzers.

The preferred contents of the mobile unit 26 are shown in greater schematic detail in FIG. 14. As seen, the tube bundle 24 entering the mobile unit 26 includes the incoming main sample tube 69, outgoing main cal gas tube 72, and outgoing main air tube 76.

Sample Analysis

In the preferred embodiment, a portion of the sample is directed through a wet analyzer 98, preferably for oxygen. The remaining sample is conditioned to remove moisture and prevent damage to the dry gas analyzers. A chilled water bath gas cooler maintained near freezing temperatures is used to quickly remove the condensed water. In the preferred embodiment, a dry analyzer 112a measuring oxygen is used with the wet analyzer 98 to derive the moisture content of the sample stream; however, another gas may alternately be used in place of oxygen.

The dry analyzers 112 measure certain pollutants, such as $SO_2$, $NO_x$ and $CO_2$. Preferred sources for the analyzers include Thermo Environmental and Western Research. The analyzers are calibrated utilizing an automatic cycling reference gas technique. This involves the injection of zero and span gases, together comprising a reference gas, directly into the sample probe and measuring the results in the analyzers. The zero or diluent gas may be nitrogen, and the span gases are cal gases at higher than zero concentrations. Each gas analyzer 98, 112 may have a sensitivity greater or less than required to accurately detect the emitted gas concentration. The known reference gas composition, available from existing CEM data, is then used to calibrate the analyzer, and also to compensate for contamination and calibrate the filter 62 located on the probe 32.

The cal gases used are of certified concentration, in accordance with EPA Protocol testing. The gases are mixed using a convention, automatic gas divider 120, thus reducing the number of gas cylinders required to be maintained in the mobile unit 26. The gas divider 120 allows a very wide range of reference gas compositions to be achieved for calibration purposes.

In the preferred embodiment of the present invention, the sample gas tube 69 is routed through both the wet analyzer 98 and a signal conditioner 100 for further analysis by the dry analyzers 112. As seen in FIG. 14, a pump 94 is used to convey the sampled gas of tube 69 through a check valve 96 to the wet analyzer 98. The sampled gas in tube 69 is conveyed through the signal conditioner 100 by a pump 102, and then proceeds through a check valve 104. A flow indicator 106, a flow switch low indicator 108, and a pressure switch 110 provide visibility as to the specific conditions of the sample gas flow prior to entry into the dry analyzers 112. The gas constituents for analysis by the dry analyzers 112 are usually well-known and conventional, and are verified prior to commencement of the testing by CEM data available from the test facility.

Diluent and cal gas cylinders 114,116a–d shown in FIG. 14 are readily transported by the mobile unit 26. The diluent gas 114 and cal gases 116a–d are routed through the gas divider 120. Solenoid valves 118a–d regulate the flow of the cal gases from the cylinders 116a–d.

Calibration and Leak Checking

During "local" calibration of the test analyzer equipment, flow continues from the divider 120 through a solenoid valve 122 and check valves 123,124. Thus, in the preferred embodiment of the present invention shown in FIG. 14, both the dry analyzers 112 and the wet analyzer 98 are calibrated.

For remote calibration of the sample tubes 68a–d, the output from the gas divider 120 is routed through a solenoid valve 126 and check valve 128, and further out through the main tube 72. Other details of the remote calibration were described above. The results of remote calibration and local calibration are compared to identify leakage and dilution of calibration gas.

Auto-Purging

Also shown in FIG. 14 is the main air tube 76 used during auto-purging by the present invention. In the preferred embodiment, an air compressor 130 may be used. The air is routed past a pressure switch 132, a solenoid valve 134, and a check valve 136 for purging of the cal gas tubes 73 via the main tube 72. The pressurized air may also be used for purging of the pitot tubes 44 or sample filter 62 when conveyed through the pressure switch 132 and a solenoid 142. The air is simultaneously routed through a regulator 138 and water gauge pressure indicator 140, then through the solenoid valve 142 for DPT calibration.

An alternate method for purging the pitot tube 44 uses an external air source 144 (typically available at the test facility), which is routed through an external air clean-up system 146. Here, the external air 144 is controlled through a valve 148 and conveyed through a filter 150, regulator 152, and pressure indicator 154 before proceeding through the regulator 138, water gauge 140, and solenoid valve 142. In either case, whether the air is from the compressor 130 or is external 144, the air line continues out of the mobile unit 26 through the tube bundle 24 via the main air tube 76. The water gauge 140 is preferably an inclined manometer, which is used to adjust the pressure control valve used in the DPT calibration mentioned above.

Computer Control

As shown in FIG. 14, the contents of the mobile unit 26 further include a PLC 156 and main computer system 158. The configuration and operation of the PLCs 92,156 in combination with the computer 158 will be described in detail below. Also located within the mobile unit 26 are a temperature transducer 157 and atmospheric pressure transducer 159 for measuring conditions within the mobile unit 26. It will be apparent to those skilled in the art that the devices and processes disclosed in FIG. 14 may be modified in alternate embodiments of the present invention.

Figure 15:
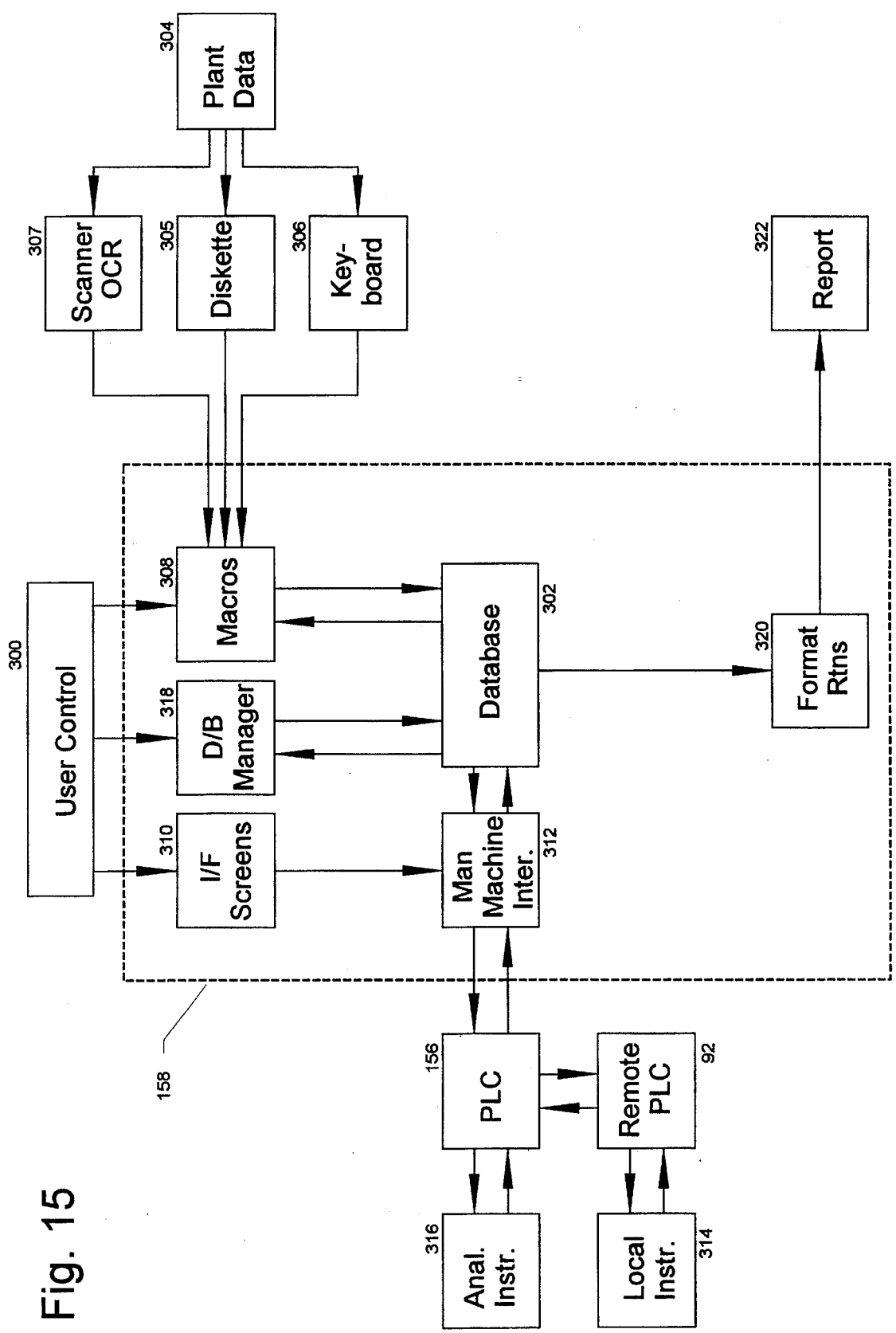
FIG. 15 is a block diagram of the data flow and control interfaces of the preferred embodiment of the present invention, illustrating the PLC connections and the input and report options.

Referring now to FIG. 15, a flow diagram of the preferred computer control of the automated system of the present invention is shown. As indicated in FIGS. 1 and 14, after the probe set 20 is temporarily installed around the smoke stack 22, the operator, via a user control 300, conducts the testing from the computer 158 located in the mobile unit 26. Access to a memory or database 302 may be initiated by inputting plant data 304, which is usually available from the facility's CEM database.

The plant data 304, typically continuous emissions data (CEM), may be graphically represented, on a computer diskette 305, or be in table form requiring manual or keyboard entry 306, and therefore pre-processing of the plant data 304 may be required. A scanner and an optical character recognition program 307 are preferably included in the present invention to input the plant data 304 from graphic representation. The user control 300 is then used to manipulate the plant data 304 via spreadsheet macros 308 resident in the computer 158.

A second option of the user control 300, shown in FIG. 15, is for the operator to utilize interface screens 310 for communicating with an MMI 312. The MMI 312 preferably allows the operator to use its own high level language to enter the necessary information, initiate operations, and format reports. The MMI 312 then communicates with the PLC 156 located in the mobile unit 26, which communicates with the remote PLC 92 located in the junction box 38. As shown in FIG. 13, the remote PLC 92 provides commands to remote devices 314 of the probe assemblies 32, and also relays data on temperature, pressure, and position back to the PLC 156. As shown in FIG. 14, the PLC 156 performs the control tasks directly for the local devices located in the mobile unit 26.

A third option of the user control 300, is to directly manipulate data through a database manager 318, as shown in FIG. 15. Thus, the information gathered and stored in the database 302 may be accessed off-line, or for training purposes, and various formatting routines 320 may be utilized to generate a report 322. The format routines 320 preferably include spreadsheets, graphics, report templates, and word processing capability. The report 322 may be a paper hard copy from a printer, or an electronic report downloaded to a diskette to be left at the test facility.

The reports represent results from testing performed by the system of the present invention, plus results from the CEM or plant data. A "relative accuracy" is the absolute value of the difference between the two results, plus the absolute value of a "confidence coefficient", divided by the average test results from the system described herein (reference method). Additional calculations performed include the determination of a "BIAS" (a factor applied to the CEM for one year), the standard deviation, and the confidence coefficient.

An embodiment of the system of the present invention can also be maintained as a backup to the CEM already in place at a company. The portability of the system does not preclude use on a stationary basis. Also, although two PLC's and a main computer are described herein, it would be obvious to combine their functions into a single computer/data logging device, possibly co-located on the stack. The potential exists for additional embodiments of this invention for soil and water testing. Other changes and modifications may be made from the embodiments presented herein by those skilled in the art without departure from the spirit and scope of the invention, as defined by the appended claims.

What is claimed is:

1. An automated gas measurement system for temporary installation at a smoke stack for performing automated flow measurement and sample collection within the interior of said smoke stack comprising:

a plurality of remotely positionable probes located within the interior of the smoke stack;

a gas sampling inlet located at substantially the proximal end of each of said probes;

a gas velocity measuring device located at substantially the proximal end of each of said probes;

a calibration gas outlet located at substantially the proximal end of each of said probes;

a temperature measuring device located at substantially the proximal end of each of said probes;

a plurality of probe positioning drivers located exterior of said smoke stack respectively operatively coupled to said probes;

a junction box located outside of said smoke stack having connections to each of said gas sampling inlets, said gas velocity measuring devices, said calibration gas outlets, and said temperature measuring devices;

a mobile unit on the ground proximate to the base of said smoke stack;

gas analysis equipment located in said mobile unit;

a computer located in said mobile unit;

a tube bundle including an air tube, a sample gas tube, and a calibration gas tube extending from said mobile unit to said junction box;

a first valve located within said junction box selectively connecting the air tube of said tube bundle to each of said gas velocity measuring devices;

a second valve within said junction box selectively connecting the gas sample tube of said tube bundle to each of said gas sampling inlets;

a third valve within said junction box selectively connecting the calibration gas tube of said tube bundle to each of said gas calibration outlets;

a first controller located within said junction box operatively connected to said plurality of drivers and said first, second, and third valves;

a second controller located within said mobile unit in communication with said first controller and said computer and operatively connected to said gas analysis equipment;

automated leak detector valves selectively actuated in sealing engagement with said gas velocity measuring device; and a report preparation apparatus responsively coupled to said computer within said mobile unit.

2. An automated gas measurement system for temporary installation at a smoke stack for performing automated flow measurement and sample collection within the interior of said smoke stack comprising:

a plurality of remotely positionable probes located within the interior of the smoke stack;

a gas sampling inlet located at substantially the proximal end of each of said probes;

a gas velocity measuring device located at substantially the proximal end of each of said probes;

a calibration gas outlet located at substantially the proximal end of each of said probes;

a temperature measuring device located at substantially the proximal end of each of said probes;

a mobile unit on the ground proximate to the base of said smoke stack;

gas analysis equipment located in said mobile unit;

a junction box located outside of said smoke stack having connections to each of said gas sampling inlets, said gas velocity measuring devices, said calibration gas outlets, and said temperature measuring devices;

a tube bundle including an air tube, a sample gas tube, and a calibration gas tube extending from said mobile unit to said junction box;

a plurality of probe positioning drivers located exterior of said smoke stack respectively operatively coupled to said probes;

a first valve located within said junction box selectively connecting the air tube of said tube bundle to each of said gas velocity measuring devices;

a second valve within said junction box selectively connecting the gas sample tube of said tube bundle to each of said gas sampling inlets;

a third valve within said junction box selectively connecting the calibration gas tube of said tube bundle to each of said calibration gas outlets;

a computer located within said mobile control unit operatively connected to (a) said plurality of drivers, (b) said first, second, and third valves, and (c) said gas analysis equipment; and automated leak detector valves selectively actuated in sealing engagement with said gas velocity measuring device.

3. An automated gas measurement system for temporary installation at a smoke stack for performing automated flow measurement and sample collection within the interior of said smoke stack comprising:

a plurality of remotely positionable probes located within the interior of the smoke stack;

a gas sampling inlet located at substantially the proximal end of each of said probes;

a gas velocity measuring device located at substantially the proximal end of each of said probes;

a calibration gas outlet located at substantially the proximal end of each of said probes;

a temperature measuring device located at substantially the proximal end of each of said probes;

a mobile unit on the ground proximate to the base of said smoke stack;

gas analysis equipment located in said mobile unit;

a junction box located outside of said smoke stack having connections to each of said gas sampling inlets, said gas velocity measuring devices, said calibration gas outlets, and said temperature measuring devices;

a tube bundle including an air tube, a sample gas tube, and a calibration gas tube extending from said mobile unit to said junction box;

a plurality of drivers located exterior of said smoke stack respectively operatively coupled to said probes;

a first valve located within said junction box selectively connecting the air tube of said tube bundle to each of said gas velocity measuring devices;

a second valve within said junction box selectively connecting the gas sample tube of said tube bundle to each of said gas sampling inlets;

a third valve within said junction box selectively connecting the calibration tube of said tube bundle to each of said calibration gas outlets; and a computer located within said mobile control unit operatively connected to said plurality of drivers and said first, second, and third valves.

4. An automated gas measurement system for installation at a smoke stack or exhaust duct for performing automated flow measurement and sample collection within the interior of said smoke stack or exhaust duct comprising:

a plurality of remotely positionable probes located within the interior of the smoke stack or exhaust duct;

a gas sampling inlet located at substantially the proximal end of each of said probes;

a gas velocity measuring device located at substantially the proximal end of each of said probes;

a mobile unit on the ground proximate to the base of said smoke stack or exhaust duct;

gas analysis equipment located in said mobile unit;

a junction box located outside of said smoke stack or exhaust duct having a plurality of connections to each of said gas sampling inlets and said gas velocity measuring devices;

a tube bundle including an air tube and a sample gas tube extending from said mobile unit to said junction box;

a plurality of drivers located exterior of said smoke stack or exhaust duct respectively operatively coupled to said probes; and a computer located within said mobile unit operatively connected to said junction box.

5. The automated gas measurement system of claim 4, wherein each of said gas velocity measuring devices is a pitot tube.

6. The automated gas measurement system of claim 4, wherein said sample gas tube provides a return line during calibration.

7. The automated gas measurement system of claim 6 having return gas flow through a bore hole proximate each of said gas sampling inlets.

8. The automated gas measurement system of claim 4, wherein each of said probes is both linearly and rotationally positionable within the interior of said smoke stack or exhaust duct.

9. The automated gas measurement system of claim 4, wherein said drivers linearly position the proximal end of each probe along generally a diametrical axis of said smoke stack or exhaust duct.

10. The automated gas measurement system of claim 4, wherein said drivers rotate the proximal end of each probe around the longitudinal axis of the probe.

11. The automated gas measurement system of claim 4 having a thermocouple located at substantially the proximal end of each of said probes.

12. The automated gas measurement system of claim 4 having a filter located at said gas sampling inlet.

13. The automated gas measurement system of claim 4, wherein each of said probes comprises a series of detachably connectable segments, each segment having an approximate length of four and one-half to seven feet.

14. The automated gas measurement system of claim 4, wherein the diameter of said smoke stack, or exhaust duct is greater than the overall length of any single probe, said system including four remotely positionable probes located in openings in the wall of said smoke stack, or exhaust duct substantially at 90° segments of the circumference of said smoke stack or exhaust duct.

15. The automated gas measurement system of claim 4, wherein the diameter of said smoke stack, or exhaust duct is substantially equal to or less than the overall length of any single probe, said system including two remotely positionable probes located adjacent each other in openings in the wall of said smoke stack or exhaust duct substantially at 90° segments of the circumference of said smoke stack or exhaust duct.

16. The automated gas measurement system of claim 4, comprising a data input device coupled to said computer, said data input device responsive to continuous emissions data.

17. The automated gas measurement system of claim 16, wherein said data input device is a scanner with optical character recognition software.

18. A method of installing a temporary system for remotely controlled emissions monitoring at a smoke stack comprising the steps of:

temporarily installing support structures outside at least two ports in the wall of said smoke stack;

detachably connecting segments for at least two remotely positionable probe assemblies such that each of said probe assemblies includes a sample collection and flow measurement assembly on its proximal end;

temporarily installing said probe assemblies into said ports;

connecting said probe assemblies to a junction box temporarily located proximate said support structures; and connecting said junction box to a mobile unit located on the ground proximate to the base of said smoke stack, wherein remote control of said emissions monitoring may be initiated and conducted from a computer located within said mobile unit.

19. A method for emissions monitoring from a remote location by a temporarily installed system at a smoke stack comprising the steps of:

temporarily installing support structures outside at least two ports in the wall of said smoke stack;

detachably connecting segments for at least two remotely positionable probe assemblies such that each of said probe assemblies includes on its proximal end a sample collection and flow measurement assembly;

temporarily installing said probe assemblies into said ports;

connecting said probe assemblies to a junction box temporarily located proximate said support structures; and connecting said junction box to a mobile unit located on the ground proximate to the base of said smoke stack;

initiating said emissions monitoring from a computer within said mobile unit, such that commands are relayed for the automatic purging and leak checking of said probe assemblies between each sample collection and flow measurement which is automatically performed at all required locations within said smoke stack;

commanding said computer to automatically prepare a report after the completion of said emissions monitoring; and removing said junction box, probe assemblies, and support structures from said smoke stack for storage in said mobile unit and transport to another emissions monitoring location.

20. An automated gas measurement system for installation at a smoke stack or exhaust duct for performing automated flow measurement and sample collection within the interior or said smoke stack or exhaust duct comprising:

a plurality of remotely positionable probes located within the interior of the smoke stack or exhaust duct;

a gas sampling inlet located at substantially the proximal end of each of said probes;

a gas velocity measuring device located at substantially the proximal end of each of said probes;

mobile gas analysis equipment;

a junction box located outside of said smoke stack or exhaust duct having a plurality of connections to each of said gas sampling inlets and said gas velocity measuring devices;

a tube bundle including an air tube and a sample gas tube extending from said mobile gas analysis equipment to said junction box;

a plurality of drivers located exterior of said smoke stack or exhaust duct respectively operatively coupled to said probes; and an electronic control apparatus and data collection device operatively connected to said junction box.

* * * * *